United States Patent [19]

Bucalo

[11] 4,325,388

[45] Apr. 20, 1982

[54] APPARATUS FOR COLLECTING AND PROCESSING BODY FLUIDS

[76] Inventor: Louis Bucalo, 155 Roberts Street, Holbrook, N.Y. 11741

[21] Appl. No.: 10,885

[22] Filed: Feb. 9, 1979

Related U.S. Application Data

[60] Continuation of Ser. No. 734,049, Oct. 20, 1976, abandoned, which is a continuation-in-part of Ser. No. 603,432, Aug. 11, 1975, Pat. No. 4,232,673, which is a continuation-in-part of Ser. No. 568,139, Apr. 14, 1975, Pat. No. 4,036,214, which is a continuation-in-part of Ser. No. 534,893, Dec. 20, 1974, Pat. No. 3,998,211, which is a continuation-in-part of Ser. No. 499,925, Aug. 23, 1974, Pat. No. 3,934,575, and Ser. No. 499,926, Aug. 23, 1974, Pat. No. 3,924,607, said Ser. No. 499,925, said Ser. No. 499,926, is a division of Ser. No. 329,862, Feb. 25, 1973, Pat. No. 3,842,166.

[51] Int. Cl.$^3$ .............................................. A61B 17/42
[52] U.S. Cl. .................................... 128/768; 128/767; 128/760; 128/749
[58] Field of Search .............. 128/769, 749, 771, 760, 128/260, 1 R, 269, 275; 195/103.5 R, 139, 140; 73/425.4 R

[56] References Cited

U.S. PATENT DOCUMENTS

| | | | |
|---|---|---|---|
| 2,702,125 | 2/1955 | Willinger et al. | 73/425.4 R |
| 3,315,660 | 4/1967 | Abella | 128/2 F |
| 3,485,235 | 12/1969 | Felson | 128/2 F |
| 3,845,770 | 11/1974 | Theeuwes et al. | 128/2 F |
| 3,874,367 | 4/1975 | Ayres | 128/766 |
| 3,886,930 | 6/1975 | Ryan | 128/766 |
| 3,924,607 | 12/1975 | Bucalo | 128/2 W |
| 3,926,521 | 12/1975 | Ginzel | 128/2 F X |
| 3,958,561 | 5/1976 | Bucalo | 128/2 F |
| 3,998,211 | 12/1976 | Bucalo | 128/2 F |
| 4,003,262 | 1/1977 | Gerarde | 73/425.4 R |
| 4,029,857 | 5/1977 | Blecher | 128/2 F |
| 4,036,214 | 7/1977 | Bucalo | 128/2 F |
| 4,172,446 | 10/1979 | Bucalo | 128/769 |

*Primary Examiner*—Robert W. Michell
*Assistant Examiner*—Nancy A. B. Swisher
*Attorney, Agent, or Firm*—Steinberg & Raskin

[57] ABSTRACT

Apparatus for purposes such as obtaining information pertaining to human beings or other animals having body cavities wherein fluids from which desired information can be derived are at least temporarily present. A means for collecting a body fluid is situated proximate to the body cavity and left there for a time sufficient to provide for collection of a quantity of fluid suitable, for example, for subsequent analysis. The fluid collected by the collecting means is enclosed in an enclosure which can then be transmitted to a laboratory or the like for subsequent analysis of the fluid.

6 Claims, 8 Drawing Figures

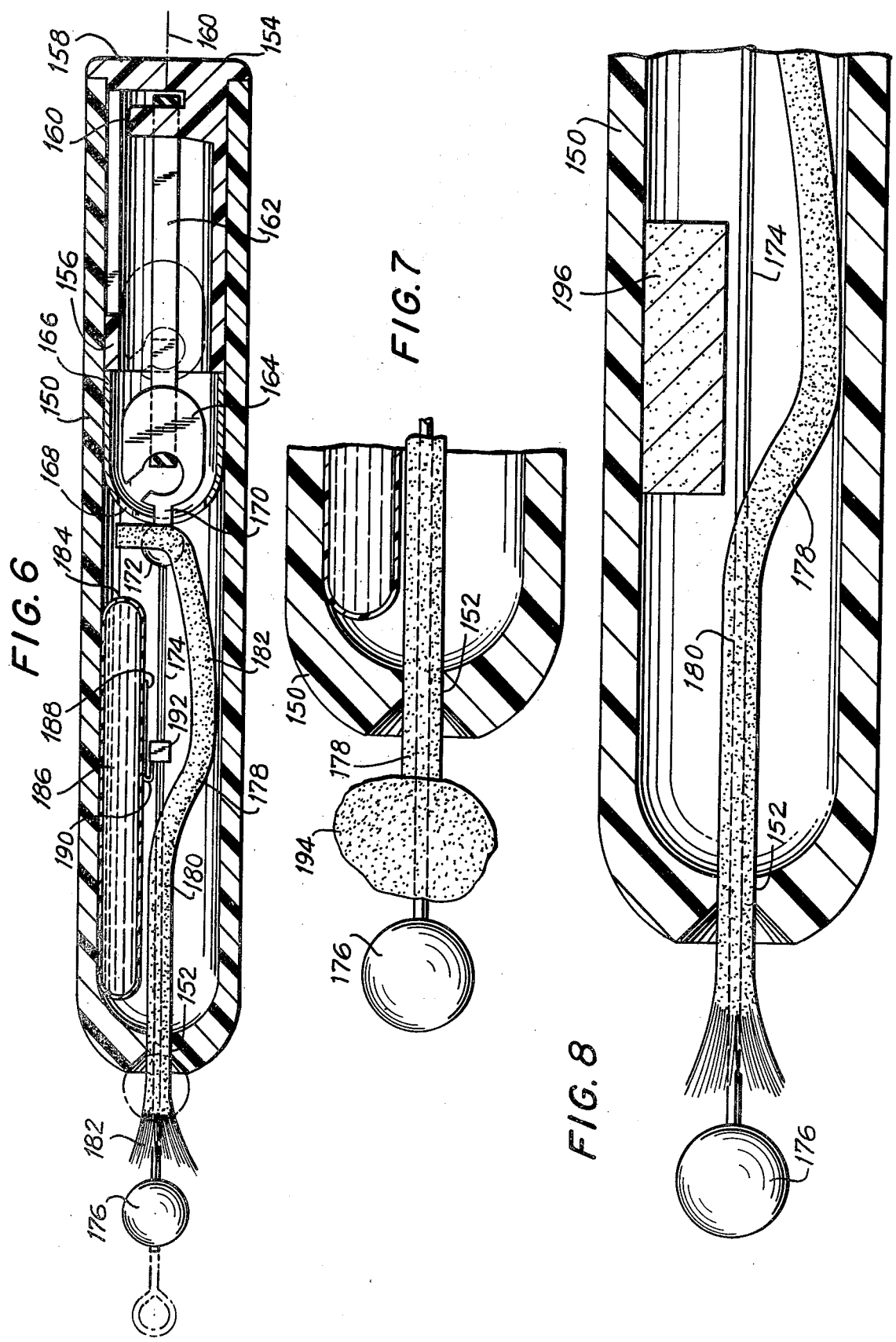

APPARATUS FOR COLLECTING AND PROCESSING BODY FLUIDS

CROSS REFERENCE TO RELATED APPLICATION

This is a continuation of Ser. No. 734,049, filed Oct. 20, 1976, now abandoned which in turn is a continuation-in-part of Ser. No. 603,432, filed Aug. 11, 1975, now U.S. Pat. No. 4,232,673 directed to the subject matter of claims not elected as a result of a requirement of restriction, which application in turn is a continuation-in-part of Ser. No. 568,139, filed Apr. 14, 1975, now U.S. Pat. No. 4,036,214, which in turn is a continuation-in-part of Ser. No. 534,893, filed Dec. 20, 1974, now U.S. Pat. No. 3,998,211, which in turn is a continuation-in-part of both Ser. No. 499,925, filed Aug. 23, 1974, now U.S. Pat. No. 3,934,575 and Ser. No. 499,926, filed Aug. 23, 1974, now U.S. Pat. No. 3,924,607 said latter two applications being divisionals of Ser. No. 329,862, filed Feb. 25, 1973, now U.S. Pat. No. 3,842,166.

BACKGROUND OF THE INVENTION

The present invention relates to apparatus for collecting fluid proximate to a body cavity, particularly the vagina, of a human being or other animal and for then treating the collected fluid in a predetermined manner.

Presently known apparatus involve certain disadvantages and inconveniences. For example where a physician feels that a patient may have a certain disease, it is common to take a swab and transmit the specimen removed by the swab to a laboratory for analysis. These procedures are not highly reliable because the removed sample is of a limited magnitude. In connection with normal menstrual flow of healthy female adults, considerable inconveniences are involved in the use of conventional tampons and sanitary napkins inasmuch as items of this type must be frequently changed.

In addition, where the presence or absence of certain diseases are to be determined, with conventional apparatus there is not only a lack of reliability as referred to above but in addition there is an unavoidable and undesirable delay in determining the results.

SUMMARY OF THE INVENTION

It is accordingly a primary object of the present invention to provide apparatus for avoiding the above drawbacks.

In particular, it is an object of the present invention to provide apparatus for collecting body fluids and enclosing the latter in a manner suitable for analysis of the collected body fluids while at the same time avoiding the possibility of causing undesirable multiplication of microorganisms in the body.

In addition it is an object of the present invention to provide apparatus of this type which will assure a rapid reliable growth of suspected microorganisms under ideal conditions even before a specimen reaches the location where an analysis thereof is to be made.

It is furthermore an object of the present invention to provide apparatus of the above type which will cause no discomfort to the human being or other animal from whom the body fluid is taken.

In addition it is an object of the present invention to provide apparatus for collecting menstrual fluid either for purposes of subsequent analysis or for the purpose of eliminating the menstrual fluid, in such a way that disadvantages inherent in conventional apparatus of this type are avoided.

According to the invention there is situated proximate to a body cavity, a means for collecting a body fluid while the latter means remains proximate to the body cavity for a length of time sufficient to provide for collection of a quantity of fluid suitable for subsequent analysis. The thus-collected fluid is enclosed in a suitable enclosure which is transmitted to a laboratory or the like where subsequent analysis takes place. The enclosure which receives the body fluid may in some cases be situated proximate to the body cavity together with the means for collecting the body fluid, and such an enclosure may be either manually or automatically closed after a suitable quantity of fluid has been collected therein. In addition, it is possible to release to the interior of the enclosure, after a suitable quantity of fluid has been collected therein, an agent which will have a desired effect with respect to the collected body fluid, such an agent being, for example, a broth in which microorganisms will rapidly grow. In connection with menstrual flow, according to the invention there may be situated proximate to the vagina a means which will collect the menstrual fluid so that the menstrual fluid can either be simply discarded or collected in a suitable container which can be sent to a laboratory for analysis of the menstrual fluid.

BRIEF DESCRIPTION OF DRAWINGS

The invention is illustrated by way of example in the accompanying drawings which form part of this application and in which:

FIG. 6 is a longitudinal sectional illustration of yet another embodiment of the invention;

FIG. 7 is a fragmentary illustration of a variation of the embodiment of FIG. 6; and FIG. 8 is a fragmentary schematic sectional view of a still further variation of the embodiment of FIG. 6.

DESCRIPTION OF PREFERRED EMBODIMENTS

Figure 1:
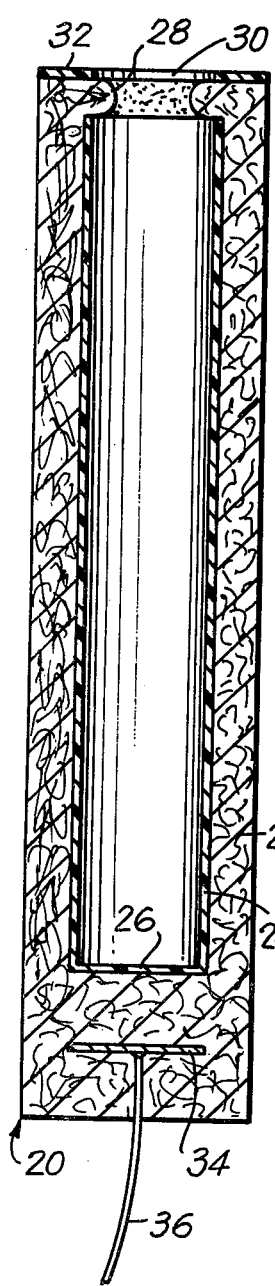
FIG. 1 is a schematic illustration of one possible embodiment of an apparatus according to the invention.

Referring now to FIG. 1, there is schematically illustrated therein an apparatus 20 according to the invention. This apparatus 20 may include an outer cushioning body 22 which may be absorbent or non-absorbent. This body 22 will enable the apparatus 20 to be situated comfortably within or at a body cavity such as the vagina, the rectum, or the like. The cushion 22 can be made of cotton wadding, or any soft plastic material which if it is desired to be absorbent can have the characteristics of a sponge.

Situated within the cushion 22 is an enclosure means 24 in the form of a container having its bottom end, as viewed in FIG. 1, closed by a suitable transverse wall 26 of the container 24. The container 24 is open at its top end as viewed in FIG. 1. Extending across this open top end of the container 24 is a wall 28 which forms part of a means for collecting fluid which is present in the body cavity. This wall 28 forms a part of the cushion 22 and extends across the open end of the container 24 while being formed with an opening 30 through which collected fluid will enter into the interior of the container 24 to remain therein. The nature of the opening 30 is such that while fluid will enter through the opening 30 into the container 24 it is highly unlikely to be discharged out of the container 24 through the opening 30 back into the body cavity. In order to promote collection of fluid through the collecting means 28 into the interior of the container 24 the outer end face of the cushion 22, which is the upper end face thereof as viewed in FIG. 1, is covered with a barrier layer 32 formed of any suitable plastic or the like which adheres to the cushion 22 and which is impervious to the fluid which is to be collected so that if the fluid engages the barrier layer 22 it will simply flow across the latter to the opening 30 of the collecting means 28 so as to be collected thereby and introduced into the container 24.

As an optional feature, the cushion 22 may have embedded therein a plate, rod, pin, or the like 34 to which one end of a pull-string 36 is attached as illustrated so that through this optional pull-string 36 it is possible to readily remove the apparatus 20 from the body cavity after it has remained therein for a length of time sufficient for collection of a suitable quantity of fluid in the container 24.

Upon such retraction from the body cavity the opening 30 can be closed as by placing a suitable tape across the barrier layer 32, or if desired the entire apparatus 20 can simply be situated in a suitable bottle or the like which can be closed and shipped with the apparatus 20 to a laboratory where the fluid in the container 24 can be tested.

It is also possible to situate in the container 24 prior to insertion of the apparatus 20 into the body cavity a suitable preservative or stabilizer such as an antibiotic or citric acid so that the received body fluid can be influenced in a manner desirable for the subsequent analysis thereof.

Figure 2:
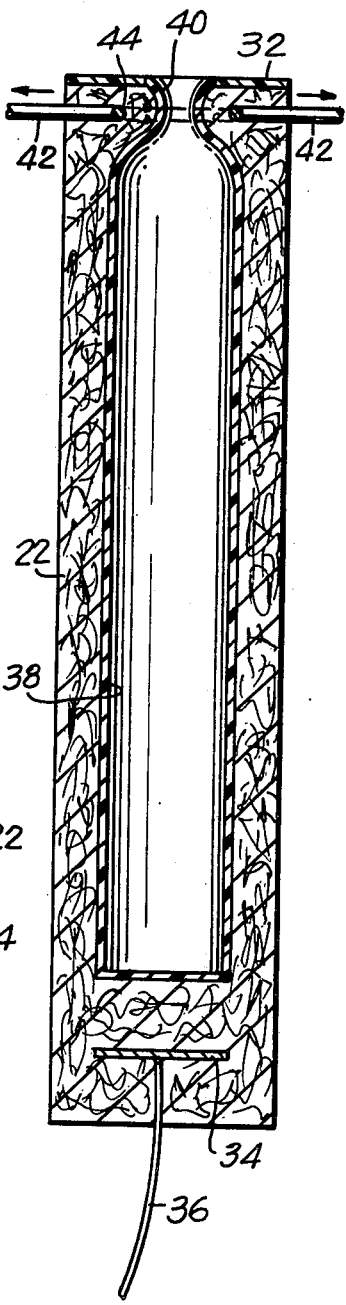
FIG. 2 is a schematic illustration of a further embodiment of an apparatus according to the invention.

The embodiment of FIG. 2 is substantially identical with that of FIG. 1, the difference being that the container 24 which forms the enclosure means of FIG. 1 is replaced by a container 36 having an upper flexible tubular wall portion 40 which initially has an open condition, as illustrated in FIG. 2, so that this wall 40 forms the means for collecting the body fluid. The wall 40 extends up to the barrier layer 32, and the entire enclosure 38 together with the collecting means 40 are situated in the cushioning element 22 which may be absorbent or non-absorbent as described above and which may have a suitable pull-string 36 connected thereto if desired. Also within the container 38 it is possible to situate a suitable preservative such as an antibiotic or the like, as referred to above in connection with FIG. 1.

With the embodiment of FIG. 2, after the device has been removed from the body cavity it is possible to close the opening 40. For this purpose a drawstring is embedded in the element 22 with a portion surrounding the wall 40 which has the opening through which the fluid enters. This drawstring can have a loop extending around the wall 40 and having opposed free ends 42 accessible to the operator for pulling so as to tightly close the loop around the wall 40 for shutting the opening formed thereby. In this way this manual closure means formed by the drawstring 44 can be manipulated to tightly close the container 38 so as to render the latter suitable for transmittal to a laboratory or the like where analysis of the collected fluid will take place.

Figure 3:
FIG. 3 is a schematic illustration of a still further embodiment of the invention.

According to the variation of the invention which is illustated in FIG. 3, the apparatus includes an outer cushioning element 46 which is optional inasmuch as the container 48 which extends partly into the cushioning element 46 may itself be made of a relatively soft film of plastic material such as polyethylene or the like which can comfortably be situated in a body cavity. Suitable plastics may have corrugated or bellows-types of wall structures giving the container 48 a flexibility rendering it highly suitable for comfortable situation in a body cavity without the use of the optional cushion 46.

Figure 4:
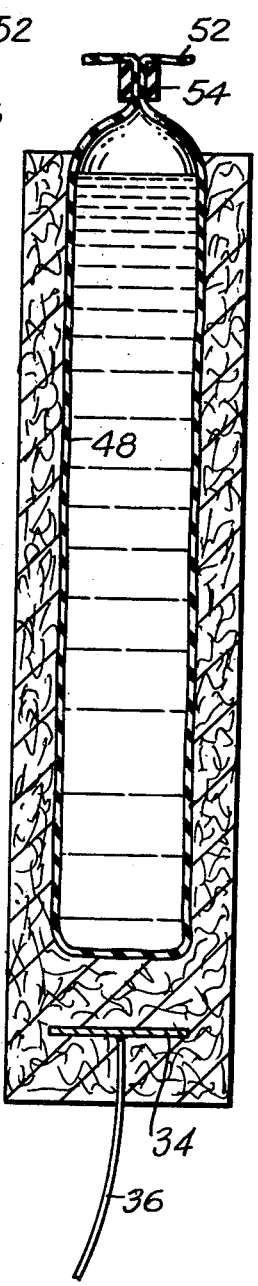
FIG. 4 shows the structure of FIG. 3 after the container with fluid therein has been closed.

The plastic material which is used for the enclosure means 48 has, as viewed in FIG. 3, an upper open end 50 forming the collecting means for collecting the fluid which is enclosed within the enclosure means 48. The flexible material of the enclosure 48 has in the illustrated example an outwardly extending flange portion 52. Adjacent the flange 52 and beyond an end of the cushion 46 there is a surrounding elastic band 54 which forms a closure means for automatically closing the opening formed by the collecting means 50 so as to close off the interior of the container 48 for retaining fluid therein which has been previously collected. In order to maintain the elastic band 54 in its expanded condition illustrated in FIG. 3 the inner surface of the upper open end region of container 48 which forms the collecting means 50 surrounds and is engaged by a substantially rigid ring 56 which is strong enough to maintain the elastic 54 in the stretched condition illustrated in FIG. 3. The ring 56 may be in the form of a dissolvable material which automatically dissolves when engaged by the body fluid, such materials being well known in the case of dissolvable sutures and the like, for example. Thus the dimensions of the ring 56 is such that it will reliably retain the collecting means 50 in the condition illustrated in FIG. 3 for a time interval sufficient for reliable collection of a suitable quantity of fluid in the container 48. When the ring 56 dissolves sufficiently either as a result of contact by the body fluid and/or as a result of exposure to the temperature prevailing in the body cavity, the ring 56 will give way so as to permit the elastic band 54 to contract to the condition shown in FIG. 4. It will be noted that this embodiment also has an optional pull-string 36 which enables the apparatus to be conveniently withdrawn from the body cavity. If desired the ring 56 can be made of a suitable plastic which does not dissolve but which has attached thereto an unillustrated string so that the operator by engaging the pull-string 36 and a string attached to a plastic or even metal ring 56 can retract the latter out of the open end 50 which forms the collecting means, thus permitting in this way the elastic 54 to contract to the condition shown in FIG. 4 for closing the container. Thus with such an embodiment it will not be necessary to enclose part of the dissolved ring 56 in the interior of the container and by manual operations it is possible to close the container 48 in the manner illustrated in FIG. 4, rendering the structure of FIG. 4 suitable for transmittal to a laboratory where the fluid in the container 48 will be analyzed. Of course in this case also within the container 48 there may be situated an agent such as a preservative, an antibiotic, a growth means, or the like.

Figure 5:
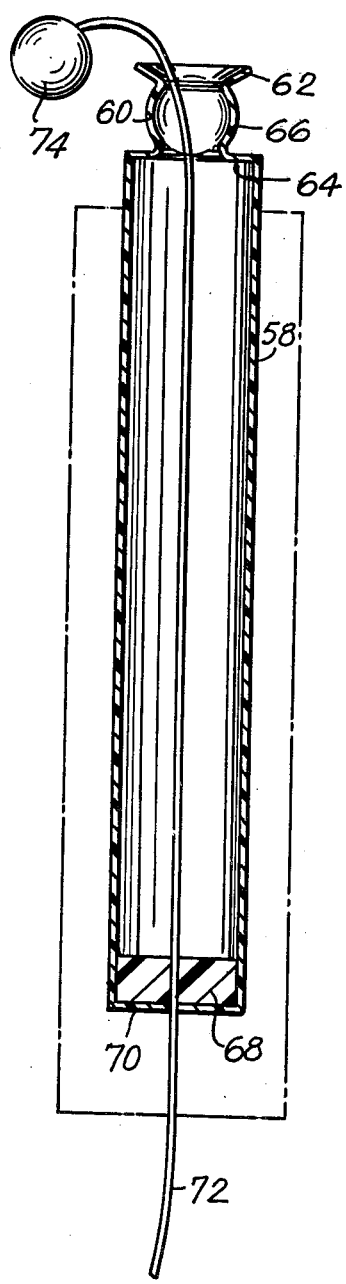
FIG. 5 shows a further embodiment of the invention according to which it is possible to close manually a container which receives a collected body fluid.

The embodiment which is illustrated in FIG. 5 also has an enclosure means formed by a container 58 made of a suitable relatively soft plastic material which can be comfortably situated in any body cavity without the use of an optional cushion which is shown in phantom lines in FIG. 5. At its upper end, as viewed in FIG. 5, the container 58 has the collecting means 60 formed by the illustrated neck of the container 58 which extends from a wall portion which extends across the interior of the container 58 and then merges into the neck 60 which has an outer flared end 62 and next to the wall portion 64 an intermediate portion 66 which has an inner concave circular surface as illustrated. At the bottom end of the container 58, as viewed in FIG. 5, is a body 68 of a suitable plastic material which directly engages the bottom wall 70 of the container 58. Extending slidably and fluid-tightly through the plastic 68 and the wall 70 is a pull-string 72 the upper end of which is connected with a closure ball 74 which normally has the position illustrated leaving the collecting means 60 in the open condition enabling collection of fluid which automatically enters into the container 58. When it is desired to terminate the collection of fluid the operator will pull the string 72 so as to displace the closure member 74 to the dot-dash line sealed position illustrated in FIG. 5 closing the collecting means 60 so that no more fluid can enter into the container 58, and further pulling of the string 72 may serve to extract the device of FIG. 5 from the body cavity. The container 58 is now in a condition for transmittal to a laboratory for analysis of the collected fluid. Of course in this case also it is possible to situate in the interior of the container any desired agent such as a suitable preservative such as an antibiotic or the like.

Referring now to the embodiment of the invention which is illustrated in FIG. 6, there is illustrated therein an elongated enclosure 150 which is made of a relatively soft and flexible material. For example the enclosure or container 150 may be made of polyethyelene. The elongated tubular container 150 forms the enclosure for receiving and enclosing the collected fluid. The left end of the container 150 is formed with an opening 152, this left end being curved so as to have the substantially hemispherical configuration illustrated. The outer end of the opening or bore 152 tapers as illustrated for a purpose referred to below.

The opposed end of the elongated tubular container 150, which is soft enough to be comfortably received in a body cavity, is open. This right end is closed by a separate closure member 154 which can be made of a suitable plastic which is bonded to the tubular container 150 so as to tightly close the right end thereof. This member 154 is itself in the form of a hollow tubular member which at its right end completely closes the container 150 while at its left end it has a ring-shaped portion 156 for a purpose referred to below. Next to the end wall portion 158 of member 154 the latter has an integral projecting portion 160 onto which one end of an elastic band 162 is hooked. The elastic band is endless and at its other end is received in a hook member 164 which also may be made of a suitable plastic.

The ring shaped portion 156 is engaged by one end of a hollow cup-shaped member 166 made of gelatin, agar, paper, or any material which can dissolve or become soft by engagement with the collected fluid or which in response to the temperature prevailing in the body will become soft and give way from the configuration illustrated in FIG. 6. This member 166 has a tubular portion directly engaging the ring 156 and extending along the inner surface of the container 150 while terminating in a hemispherical portion formed with an elongated slot 168 through which a flat band-shaped portion 170 of a plastic extension of the hook member 164 extends. The member 164 is a simple flat body of plastic formed with a substantially keyhole-shaped slot which receives the end of the elastic band 162 as illustrated. The flat portion 170 which extends through the slot 168 is integral with a ball member 172 also made of a suitable plastic in the same way as the parts 164 and 170, and this ball member 172 has a diameter too large to pass through the slot 168 so that this construction maintains the elastic band 162 in its tensioned stretched condition illustrated in FIG. 6.

The ball 172 is integral with an elongated tie-rod or retractor element 174, which simply takes the form of an elongated filamentary body of the same plastic material as the elements 172, 170, and 164. This elongated filamentary retractor element 174 extends freely through the opening 152 to the exterior of the container 150 where the filamentary element 174 is integrally formed with a sealing ball member 176 which serves to close the opening 152 in a manner described in greater detail below. Initially the sealing or closure member 176 is situated well beyond the opening 152 in a manner illustrated in FIG. 6.

The means for transferring the fluid in the embodiment of FIG. 6 also operates by capillary motion and takes the form of an elongated wick 178 which can be made of a suitable braided filamentary cotton or other material. It is possible, however, also to make the wick in the form of a simple capillary tube. In some cases the opening alone may be sufficient for collection, so that a wick is unnecessary. An elongated portion 180 of the wick passes through the opening 152 as illustrated. The tie-rod or retractor element 174 also extends along the interior of this portion 180 of the wick. At its outer end which is situated outwardly beyond the container 150 the wick has a frayed end 182 for facilitating collection of the body fluid. Between the ball member 172 and the portion 180 the wick has a portion 182' which is curved as illustrated so as to be separated from the interior portion of the filamentary element 174 where it is joined to the interior ball member 172, and the right free end of the wick 178 is situated as illustrated around part of the ball member 172 and next to the curved end of element 166 which is formed with the slot 168.

In accordance with a further feature of the invention there is joined by any suitable adhesive or the like to the interior surface of the container 150 an inner flexible bag 184 which contains in its interior an agent which is to be released to the interior of the container 150. This inner bag 184 or the like may contain a preservative such as an antibiotic agent, or a suitable broth in which microorganisms will rapidly grow. It has been found from experience that some microorganisms will grow much more rapidly in a liquid medium, and such a liquid medium may be located in the bag 184. This bag 184 is also made of any suitable plastic such as a thin polyethylene film. The bag 184 with the agent 186 therein, which may be even plain water or a simple saline solution if desired, is thus mounted in the interior of the container 150 in the manner illustrated. This bag 184 has an elongated tear strip portion 188 which when removed will release the contents of the bag 184 to the interior of the container 150. This tear strip portion 188 is integrally fixed with an extension 190 which terminates in a thicker portion 192 which surrounds and is fixedly bonded to the plastic filamentary retractor element 174.

When the embodiment of FIG. 6 is introduced into the body cavity the frayed end 182 of the wick 180 which forms the fluid-transfer means will engage the fluid which is to be collected and the fluid will by capillary action be sucked along the wick 180 so as to saturate the latter with the fluid, and this fluid will of course come into engagement with the curved end of element 166 which is formed with the slot 168. This element 166 forms a trigger means which in response to engagement with the collected liquid and/or in response to the temperature of the body softens and gives way either by dissolving or crumpling or the like so as to release the tension in the elastic 162 which at this time will pull the element 164 toward the projection 160 as the elastic band 162 contracts. The result is that the wick 178 as a result of the connection of its portion 180 to the retractor element 174 becomes automatically pulled into the interior of the container 150 after a suitable quantity of fluid has been collected in the latter. In addition, as the retractor portion 174 moves to the right in response to contraction of the elastic band 162, the parts 190 and 192 act to tear the tear strip portion 188 from the bag 184 so as to open the latter and release the agent 186 to the interior of the container so that this agent will now cooperate with the collected fluid for purposes such as preserving the latter, growing microorganisms which may be present in the fluid, or if there is an antibiotic forming at least part of the agent 186 certain undesirable microorganisms, if they are present, will be inhibited by the antibiotic agent.

At the same time, the retraction of the portion 174 by the contraction of the elastic 162 will serve to displace the closure member 176 into engagement with the tapered portion of the opening 152 so as to tightly close this opening and thus prevent any escape of material from the container 150 while at the same time terminating further admission of material to the interior thereof. The container 150 can then of course be removed from the body, although it may be left to remain in the body for a time sufficient for microorganisms, if they are present, to grow under the conditions prevailing in the interior of the body. For convenience of removal the wall 158 of the element 154 can have a pull-string 160 attached thereto.

It is to be noted that with the embodiment of FIG. 6, if upon removal of the device it has the condition shown in FIG. 6, it is immediately known that for some reason the triggering action did not take place and that in fact no fluid was collected, for example because the device was improperly positioned. Therefore, with this device there is an assurance that there will be no false or unnecessary checking for fluid which has not even been collected. If the device is removed and still has the condition shown in FIG. 6, then of course it can be reinserted and properly positioned.

According to the variation of the embodiment of FIG. 6 which is shown in FIG. 7, the wick 178 instead of having a frayed end 182 is connected beyond the container 150 with a ball 194 of cotton or the like which greatly facilitates the collection of the fluid. The ball of cotton 194 is soft enough so that it can be pulled together with the remainder of the wick through the opening 152 in the manner described above, and of course then the closure element 176 will seal the opening 152.

In the embodiment of the invention which is illustrated in FIG. 8, the structure is identical with that of FIG. 6 except that there is no flexible bag 184 with an agent therein. Instead a block 196 is fixed to the inner surface of the container 150 as illustrated. This block 196 is in the form of a relatively solid agar having a nutrient medium, as is well known, for microorganisms which may be present in the collected fluid. It will be noted that the position of the block 196 with respect to the wick 178 is such that when the wick 178 is retracted by the retractor element 174, the portion 180 of the wick will necessarily rub across the block 196 so as to deposit in a highly reliable manner a specimen of fluid on the agar element 196 so that the nutrient in the agar will bring about desired growth and culturing of microorganisms if they are present in the fluid. Thus, by examining the block 196 after a sufficient time it is possible to determine whether or not certain microorganisms are present. For this purpose it may be possible to introduce suitable dyes with a syringe needle through the wall of the container 150 or the latter may simply be broken away to render the block 196 accessible for checking as to whether or not colonies of suspected microorganisms have grown.

It is apparent, therefore, that with the present invention it is possible to situate proximate to a body cavity a structure which while being extremely comfortable at the same time will reliably collect body fluid in such a way that the collected fluid cannot be returned to the body cavity. This collected fluid can be treated in a variety of ways to enable desired information to be derived from the collected body fluid. Also it is possible as was pointed out above to greatly improve the manner in which menstrual blood is collected.

In this latter connection it is to be noted that in accordance with the present invention it is also possible upon removal of a conventional tampon during menstrual flow to squeeze or flush and squeeze the collected menstrual fluid into a container and then send the container to a laboratory or the like so that the collected fluid can be treated. In the alternative it is also possible to place the removed tampon with the collected fluid therein in its entirety in a container for transmittal to a laboratory for testing purposes. In either of these latter embodiments of the present invention it is possible to situate in the container which receives either the fluid from the tampon or the entire tampon with the fluid therein a suitable preservative such as an antibiotic or the like.

In the above-described embodiments of the invention it is possible to include in any of the above enclosures with the collected fluid not only a suitable preservative such as citric acid or an antibiotic, but in addition it is also possible to include a suitable diluting agent, which in many cases may be water, so that the collected fluid will have a desired concentration suitable for subsequent analysis or for certain functions such as action of an antibiotic or the like.

Of course, it is to be understood that when any of the above embodiments of the invention is removed from a given collection site, it is provided with suitable identification so that a specimen which is analyzed can be accurately related to a given individual, thus preventing transmission of information in connection with a specimen to an individual from whom the specimen was not taken. Such identification may be in the form of a suitable adhesive tape or the like which is attached to the exterior of the device and which bears on it identifying indicia such as the name of the individual, an identifying number, or the like.

Furthermore, when a specimen is to be checked it can first be subjected to treatments such as agitation, exposure to ultrasonic waves, centrifuging, filtering or the like, in order to place the specimen in a condition suitable for analysis.

It is to be understood that in the above description and the claims which follow the term "vaginal fluid" is intended to include not only menstrual blood but also any discharge which may be collected in the vagina, such as discharges which may be received at the cervix from the uterus, or mucous or other fluids found in or near the vagina and capable of being tested to indicate vaginitis. As is well known, the discharges such as menstrual blood will include endometrium and the tests which are carried out during analysis may be used to indicate the presence or absence of diseases such as gonorrhea or cancer. Thus, the term "vaginal fluid" is intended to include all such materials, even solid particles which are suspended in the collected fluid, while "menstrual blood" is intended to signify not only blood per se but rather the entire discharge during menses, including endometrium, cells, microorganisms, mucous, etc.

Particularly in the case of menstrual blood, one of the important treatments according to the present invention in connection with analysis resides in diluting the menstrual blood with a suitable amount of water so that the red blood cells previously suspended in the menstrual blood will settle after expansion, as is well known with other blood taken from the body of a human being, animal, or the like. It has been found that when menstrual blood is diluted in this way, after the red blood cells have settled the solution still has suspended therein all other cells, microorganisms, particles, and the like such as endometrium particles, cancer cells, etc. Thus, by treating menstrual blood in this way it is possible to obtain very easily a solution from which a part may be removed and placed on a slide for suitable examination under a microscope, for example. Thus, by diluting menstrual blood with a suitable amount of water it is possible to obtain in the solution which has no red blood cells therein in a highly convenient manner a specimen suitable for analysis for presence or absence of certain diseases as pointed out above.

It is at the present time known to take a smear from the cervix or other areas accessible to the vagina and to check such a specimen for the presence or absence of certain diseases. These procedures, however, involve a certain amount of inconvenience in that the specimen must be placed on a suitable slide, and then it must be dried, it must have suitable dyes applied thereto, and then when situated between a pair of slides it is examined under a microscope. In connection with the well known Pap test for cancer, some 30 different steps are required in order to determine the presence or absence of cancer.

It has been found most surprisingly in accordance with the present invention that procedures of this type can be considerably simplified because the solution which remains after the red blood cells of the menstrual blood have settled out of the solution is extremely rich in endmetrium and cells which may be cancer cells. For example, according to the invention in one specific procedure 2 cc of menstrual blood are diluted with 4 cc of distilled water, at room temperature, and after some slight agitation, the solution is allowed to stand for a period of only 5 minutes, after which the red blood cells settle to the bottom of the solution. The liquid which remains is extremely rich in cells which may possibly be cancer cells, and as a result of this fact it is possible to greatly simplify presently known procedures for detection of uterine cancer. Thus, a part of this remaining liquid may be applied as a film to a slide and treated in a conventional manner for detection of presence or absence of cancer cells. However it is also possible simply to filter the liquid remaining after the red blood cells of the menstrual blood have settled out of the solution. Through such filtering it is possible to collect a mass of matter in which cancer cells, for example, if they are present will be present in such numbers that by utilizing dyes which are normally used for conventional detection of the presence or absence of cancer cells it is possible to provide the mass remaining after filtration with a suitable dye so that simply by inspecting the color of this remaining mass or the color of a solution into which the dyed material has been placed it is possible to detect the absence or presence of cancer without the presently known complications. Of course the material remaining after filtration can, if desired, first be placed into a solution and then such a solution may be provided with a suitable dye so that if cancer cells are present they will in a known way provide an indication by color of the presence or absence of cancer.

Procedures of this type particularly in connection with a solution from endometrium or cervix cells contained in the liquid remaining after the red blood cells have settled makes it possible to utilize automatic procedures for detecting the presence or absence of uterine cancer. For example either part of the solution remaining after settling of the red blood cells from the menstrual blood or the matter which has been filtered from the solution and itself placed in the solution can be treated with a suitable dye, and thereafter the liquid can be processed through known devices for automatically detecting the presence or absence of certain colors in a highly accurate manner so that through such automatic procedures the presence or absence of cancer can be detected. For example there are known colorimeters in which light passing through a suitable optical system is also passed through the solution which is to be tested, with suitable photocells or the like responding to given wave lengths so as to pick up in a highly accurate manner signals which are processed for indicating automatically whether or not certain colors indicative of the presence or absence of certain diseases are present. Such devices can be used with the materials derived from the menstrual blood in accordance with the present invention so as to detect the presence or absence of uterine cancer in a manner which is far more efficient and less costly than presently known methods.

In connection with preservatives in the form of antibiotics which can be utilized either before or after fluid collection, it is to be noted that a solid preservative can be utilized. Such a solid, chloramphenicol for example, can be situated in the container in which fluid is to be collected prior to fluid collection so that only upon contact by the collected liquid will the solid preservative dissolve to provide the preservative action. However it is also possible to introduce such a solid antibiotic substance, in suitable pellet form, for example, into the collected fluid after it is collected as, for example, into the container in which the collected fluid is transmitted to a laboratory or the like for analysis.

It is to be noted that, as is apparent from the above description, according to the present invention a noninvasive collection system is utilized in that according to the invention there is no interference with normal body functions and no procedure such as scraping or the like to remove tissue are involved.

Also, in connection with the above description it is to be noted that the term "microorganisms" is intended to include bacteria, fungi, and viruses, without necessarily being restricted only to the latter types of microorganisms.

What is claimed is:

1. In an apparatus for obtaining from a female body fluid, such as vaginal fluid, information pertaining to female human beings or other female animals, collecting means for automatically collecting a body fluid when in contact with the same, said collecting means being capable of remaining comfortably in juxtaposition to a body cavity, such as the vagina, for a time sufficient for collecting a body fluid, such as vaginal fluid, in an amount sufficient for analysis, enclosure means for enclosing the collected fluid for transmittal to a laboratory or the like where the collected fluid is to be analyzed, said enclosure means having an interior with which said collecting means communicates, means for causing said body fluid to flow from the collecting means to the enclosure means while substantially avoiding flow of the collected fluid by way of the collecting means back to the body cavity, and closure means operatively connected to said enclosure means for closing said enclosure means not later than upon removal of the same from the body cavity so as to prevent contamination of body fluid in the enclosure means.

2. The combination of claim 1 and wherein an agent such as a preservative is situated in said enclosure means for cooperating with the collected fluid to give a desired characteristic to the latter.

3. In an apparatus for obtaining information pertaining to human beings or other animals having body cavities wherein fluids from which the desired information can be derived are at least temporarily present, collecting means for automatically collecting a body fluid when said collecting means is situated in juxtaposition to a body cavity where the fluid is present, enclosure means for enclosing the collected fluid for transmittal to a laboratory or the like where the collected fluid is to be analyzed, said collecting means and enclosure means being provided with means for causing flow of the fluid from the collecting means to the enclosure means while substantially avoiding flow of the collected fluid by way of the collecting means back to the body cavity, said collecting means operating by capillary action to automatically collect fluid in the body cavity, said collecting means being in the form of a unit such as a wad of filamentary material, and said enclosure means including a container into which said collecting means partly extends for delivering collected fluid thereto, and closure means operatively connected to said enclosure means for closing said enclosure means not later than upon removal of the same from the body cavity so as to prevent contamination of body fluid in the enclosure means.

4. In an apparatus for obtaining information pertaining to human beings or other animals having body cavities wherein fluids from which the desired information can be derived are at least temporarily present, collecting means for automatically collecting a body fluid when said collecting means is situated in juxtaposition to a body cavity where the fluid is present, and enclosure means for enclosing the collected fluid for transmittal to a laboratory or the like where the collected fluid is to be analyzed, said collecting means and enclosure means being provided with means for causing flow of the fluid from the collecting means to the enclosure means while substantially avoiding flow of the collected fluid by way of the collecting means back to the body cavity, said collecting means including an elongated wick adapted to automatically suck body fluid from an end of the wick in engagement with the body fluid along the length of the wick, said enclosure means including an elongated enclosure formed with an opening through which the wick extends into the interior of the enclosure, trigger means in the enclosure for automatically retracting the wick into the interior of the enclosure after the enclosure and wick have remained in juxtaposition to the body cavity for a time sufficient to afford collection of a suitable quantity of fluid by the wick, means responding to operation of the trigger means to retract the wick into the enclosure for automatically placing in engagement with the fluid collected by the wick an agent which affects the fluid, and closure means operatively connected to said enclosure means for closing said enclosure means not later than upon removal of the same from the body cavity so as to prevent contamination of body fluid in the enclosure means.

5. The combination of claim 4 and wherein a closure means is operatively connected with said trigger means to be actuated thereby for automatically closing said opening to the exterior of the enclosure.

6. The combination of claim 4 and wherein said trigger means has a temperature-responsive component which in response to the temperature of the body cavity responds to cause the trigger means to retract the wick after the enclosure and wick have been at the body cavity for a length of time sufficient for collection of a suitable quantity of the fluid.

* * * * *